(12) United States Patent
Mash et al.

(10) Patent No.: US 12,226,488 B2
(45) Date of Patent: Feb. 18, 2025

(54) NITROREDUCTASE-RELEASABLE PRO-DRUGS AND METHODS FOR USING THE SAME

(71) Applicant: Arizona Board of Regents on Behalf of the University of Arizona, Tucson, AZ (US)

(72) Inventors: Eugene A. Mash, Tucson, AZ (US); Pawel R. Kiela, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 682 days.

(21) Appl. No.: 17/601,767

(22) PCT Filed: Apr. 6, 2020

(86) PCT No.: PCT/US2020/026961
§ 371 (c)(1),
(2) Date: Oct. 6, 2021

(87) PCT Pub. No.: WO2020/210175
PCT Pub. Date: Oct. 15, 2020

(65) Prior Publication Data
US 2022/0211854 A1    Jul. 7, 2022

Related U.S. Application Data

(60) Provisional application No. 62/830,532, filed on Apr. 7, 2019.

(51) Int. Cl.
| | | |
|---|---|---|
| C07H 15/26 | (2006.01) | |
| A61K 47/54 | (2017.01) | |
| C07H 19/06 | (2006.01) | |
| C07H 19/073 | (2006.01) | |

(52) U.S. Cl.
CPC ........... *A61K 47/549* (2017.08); *C07H 15/26* (2013.01); *C07H 19/06* (2013.01); *C07H 19/073* (2013.01)

(58) Field of Classification Search
None
See application file for complete search history.

(56) References Cited

U.S. PATENT DOCUMENTS

| | | |
|---|---|---|
| 2008/0085871 A1 | 4/2008 | Tam |
| 2011/0144066 A1 | 6/2011 | Mahadevan |
| 2018/0125875 A1 | 5/2018 | Matsumoto |

FOREIGN PATENT DOCUMENTS

| | | | |
|---|---|---|---|
| JP | 2001264660 | 9/2001 | |
| JP | 2002350757 | 12/2002 | |
| JP | 2006162731 | 6/2006 | |
| JP | 5669610 | 2/2015 | |
| JP | 2017009758 | 1/2017 | |
| WO | 2017218537 | 12/2017 | |
| WO | WO-2017218357 A1 * | 12/2017 | ............. B01D 35/02 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al., "Modern Pharmaceutics, 3ed.", Marcel Dekker, New York, 1996, p. 596 (Year: 1996).*
Oliveira, et al., "Nitroreductases: Enzymes with Environmental, Biotechnological and Clinical Importance", Current Research, Technology and Education Topics in Applied Microbiology and Microbial Biotechnology, Formatex, (2010).
Rafii, et al., "Role of reductive enzymes from human intestinal bacteria in the metabolism of azo dyes and nitro-polycyclic aromatic hydrocarbons", Microecology and Therapy, 23:111-123 (1995).
Ruiz, et al., A nitrophenyl-based prodrug type for colorectal targeting of prednisolone, budesonide and celecoxib, Bioorg. Med. Chem. Lett., 23:1693-1698 (2013).
Searle, et al., "Nitroreductase: a prodrug-activating enzyme for cancer gene therapy", Clinical and Experimental Pharmacology and Physiology, 31:811-816 (2004).
Zachariah, et al., "The role of gut flora in the reduction of aromatic nitro-groups", Drug Metabol. Disp., 2:74-78 (1974).

* cited by examiner

*Primary Examiner* — Traviss C McIntosh, III
(74) *Attorney, Agent, or Firm* — PABST PATENT GROUP LLP

(57) ABSTRACT

The present invention provides a nitroreductase-releasable pro-drug of the formula:

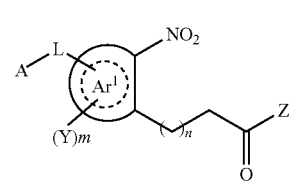

where $Ar^1$, m, n, Z, Y, L, and A are as defined herein, and methods for using and producing the same. Compound of formula I is useful in oral administration of the active pharmaceutical ingredient to the distal gut region of a subject to treat a wide variety of clinical conditions associated with distal gut region of a subject, such as colorectal cancer, inflammatory bowel disease (IBD), infectious diarrhea, bacterial infections, and bacterial overgrowth.

20 Claims, No Drawings

NITROREDUCTASE-RELEASABLE PRO-DRUGS AND METHODS FOR USING THE SAME

CROSS-REFERENCE TO RELATED APPLICATIONS

This application is a U.S. National Stage Patent Application under 35 U.S.C. § 371 of PCT Patent Application No. PCT/US20/26961, filed Apr. 6, 2020, which claims the priority benefit of U.S. Provisional Application No. 62/830,532, filed Apr. 7, 2019, which is incorporated herein by reference in its entirety.

FIELD OF THE INVENTION

The present invention relates to methods and pro-drugs that are administered orally to deliver the active pharmaceutical ingredient to the colon or the distal-gut of a subject. The pro-drugs of the invention are designed such that nitroreductase that is present in the distal gut of a subject cleaves and releases the active pharmaceutical ingredient. In particular, the compounds or the pro-drugs of the invention include an aromatic or heteroaromatic moiety having a nitro group that is present ortho to the pro-drug moiety such that reduction of the nitro group to an amine results in cleavage of the pro-drug moiety and release of the active pharmaceutical ingredient.

BACKGROUND OF THE INVENTION

Colorectal cancer is the second leading cause of cancer-related deaths in the United States. It is estimated that approximately 140,000 new cases of colorectal cancer are diagnosed annually. It is also estimated that about 56,000 people will die from the disease this year. Colorectal cancer surpasses both breast cancer and prostate cancer in mortality. In fact, colorectal cancer is second only to lung cancer in numbers of deaths in the United States. Colorectal cancer strikes men and women with almost equal frequency.

Typically, a lifetime risk of an individual for developing colorectal cancer is about 5 percent. However, someone whose family has a history of colorectal cancer has a 10 to 15 percent chance of developing the disease. The risk rises to over 50 percent in people with ulcerative colitis and those whose family members harbor specific genetic mutations.

The risk of developing colorectal cancer increases with age. All men and women aged 45 and older are at a higher risk for developing colorectal cancer. Thus, it is recommended that colorectal cancer screening be performed starting at age 45. However, because individuals with a personal or family history of inflammatory bowel disease, colorectal cancer or polyps, or ovarian, endometrial or breast cancer have a higher risk of developing colorectal cancer before the age of 45, it is recommended that these individuals begin colorectal cancer screening before the age of 45.

Some ethnic groups, such as African Americans and Hispanics, are more likely to be diagnosed with colorectal cancer in advanced stages. In fact, Alaska Native women have the highest mortality from colorectal cancer of any other racial and ethnic group in the United States.

5-Fluorouracil (5-FU) is often the drug of choice for colorectal cancer treatment. Chemotherapy in general, including 5-FU treatment, can lead to common and debilitating adverse effects such as hair loss, mouth sores, loss of appetite, nausea and vomiting, diarrhea, increased chance of infections (e.g., due to reduced white blood cell count), easy bruising or bleeding, and fatigue. Systemic 5-FU treatment can also specifically lead to the hand-foot syndrome, neuropathy, or allergic or sensitivity reactions when used in combination with other anti-cancer drugs. Studies have shown that oral administrations of pro-drugs for 5-FU (e.g., capecitabine and tegafur) have advantages over IV administration of the drug itself, including: longer 5-FU exposure at lower peak concentrations, leading to improved therapeutic activity; lower administration costs; and reduced toxicity-related hospitalization. However, capecitabine and tegafur must be metabolized in the liver before 5-FU can be released, thus, the drug is not concentrated in the colon, but rather is systemically available. This leads to adverse effects which might be avoided if 5-FU was specifically released in the colon and remained concentrated there. Currently, there is no therapeutic treatment that can be used orally to deliver 5-FU or other colorectal cancer treatment drugs specifically to the colon.

Therefore, there is a need for a method that allows release of 5-FU or other active pharmaceutical ingredients in the colon.

SUMMARY OF THE INVENTION

The present invention is based at least in part on drug release by enzymes present in the gastrointestinal tract of a subject to deliver via an oral administration an active pharmaceutical ingredient or a drug, such as 5-fluorouracil, for the targeted treatment of various clinical conditions occurring in the gastrointestinal tract. In one particular embodiment, the compounds of the invention are used to deliver a drug or a pro-drug to the colon or rectum of a subject. Such compounds and methods provide increased clinical efficacy, half-life, and/or bioavailability while reducing systemic exposure and the accompanying adverse effects.

One particular aspect of the invention provides a nitroreductase-releasable pro-drug of the formula:

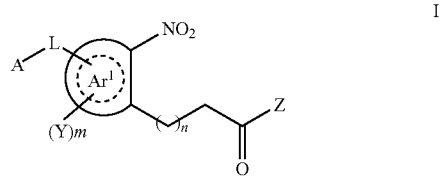

where
- $Ar^1$ is aryl or heteroaryl;
- m is an integer from 0 to (t−3), wherein t is a total number of substituents possible on $Ar^1$;
- n is 0 or 1;
- Z is a pharmaceutically active compound or a prodrug thereof,
- Y is halide, alkyl, alkoxy, acetoxy, phenyl, or —N=N-Phenyl;
- L is a linker; and
- A is a carbohydrate.

In some embodiments, the nitroreductase-releasable pro-drug is capable of releasing the pharmaceutically active compound in the distal gut of the subject. Yet in other embodiments, when the nitroreductase-releasable pro-drug is orally administered to a subject, at least about 80%, typically at least about 85%, often at least about 90%, and more often at least about 95% of the nitroreductase-releasable pro-drug passes through the stomach of the subject.

In one particular embodiment, $Ar^1$ is an aryl. Exemplary aryls that are useful in the invention include, but are not limited to, phenyl, anthracenyl, phenanthracenyl, and naphthalenyl. In other embodiments, $Ar^1$ is heteroaryl. Exemplary heteroaryls that are useful in the invention include, but are not limited to, pyridinyl, furanyl, thiophenyl, pyrimidinyl, imidazoyl, and oxazolyl.

In another embodiment, n is 1. Yet in another embodiment, n is 0.

In further embodiments, the pharmaceutically active compound comprises a drug for treating colorectal cancer, stomach cancer, inflammatory bowel disease (IBD), infectious diarrhea, intestinal bacterial infection, or intestinal bacterial overgrowth. In one particular embodiment, Z is an anticancer agent.

Yet in other embodiments, Z is selected from the group consisting of 3-indolepropionic acid, 5-aminosalicylic acid, acetylsalicylic acid, budesonide, celecoxib, 5-fluorouracil, folinic acid, irinotecan, metformin, metronidazole, prednisolone, regorafenib, salicylic acid, 2'-deoxy-5-fluorouridine, and a derivative thereof.

In one particular embodiment, L is a moiety of the formula:

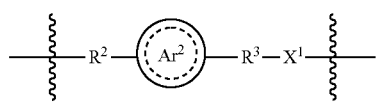

II where
$Ar^2$ is aryl or heteroaryl;
each of $R^2$ and $R^3$ is independently alkylene or heteroalkylene; and
$X^1$ is O, S, or $NR^1$, wherein $R^1$ is hydrogen, alkyl, aryl, aralkyl, heteroalkyl, cycloalkyl, cycloalkylalkyl, or oxygen.

In some embodiments, $R^2$ is $C_{1-8}$ alkylene or $C_{2-8}$ heteroalkylene and $R^3$ is $C_{2-12}$ alkylene or $C_{2-12}$ heteroalkylene.

Yet in other embodiments, $Ar^2$ is heteroaryl. In some instances, $Ar^2$ is triazolyl.

Still in other embodiments, A is a mono- or a disaccharide. In one particular embodiment, A is a carbohydrate selected from the group consisting of:

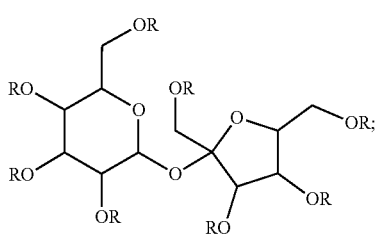

A

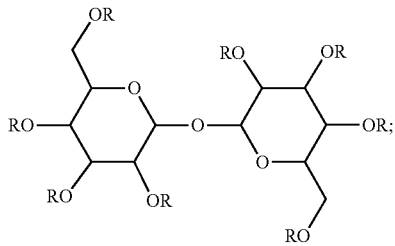

B

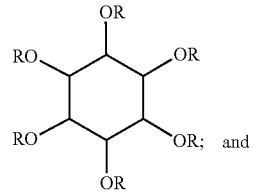

C

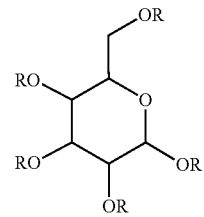

D where each R is independently hydrogen, a hydroxy protecting group (e.g., acyl groups of the formula —C(=O)—$R^a$, where $R^a$ is alkyl, cycloalkyl, aryl, aralkyl, etc.), an alkyl, or a moiety of the formula:

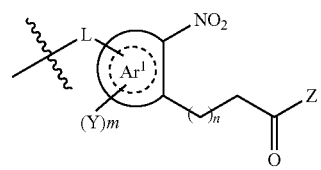

III wherein $Ar^1$, m, n, L, Y, and Z are those defined herein, provided at least one of R is a moiety of formula III.

In some embodiments, at least two R, typically at least five R, often at least six R, more often at least seven R, and most often all R are moieties of formula III.

Another aspect of the invention provides a method for treating colorectal cancer in a subject in need of such a treatment by orally delivering a therapeutically effective amount of a nitroreductase-releasable pro-drug of Formula I, where Z is 5-fluorouridine or 5-fluorouracil.

In some embodiments, the amount of systemic release of the pharmaceutically active compound is reduced by at least about 30%, typically by at least about 50%, and often by at least about 70% by using the nitroreductase-releasing pro-drug of Formula I compared to another active form of the pharmaceutically active compound. In this manner, it is believed that side-effects associated with treatment of colorectal cancer can be significantly reduced.

Another aspect of the invention provides a method for reducing side-effects in oral administration of 5-fluorouracil in treatment of colorectal cancer in a subject by administering to the subject in need of such a treatment a nitroreductase-releasable pro-drug of 5-fluorouracil. The method is based at least in part on a theory by the present inventors that orally administering to the subject in need of colorectal cancer treatment, a nitroreductase-releasable 5-fluorouracil pro-drug allows the release of the 5-fluorouracil in the distal gut (e.g., colon or rectum) region of the subject. In some embodiments, the nitroreductase-releasable pro-drug of 5-fluorouracil is of the formula:

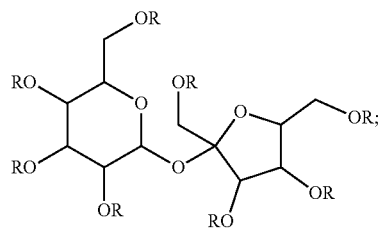
A

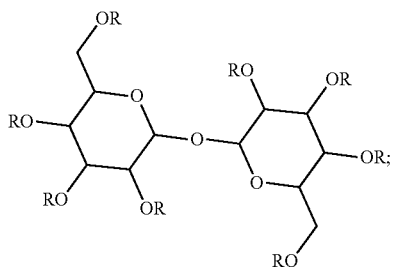
B

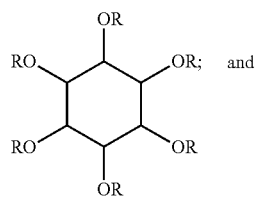 and
C

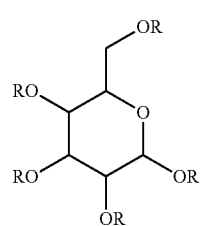
D where each R is independently hydrogen, a hydroxy protecting group, an alkyl, or a moiety of the formula:

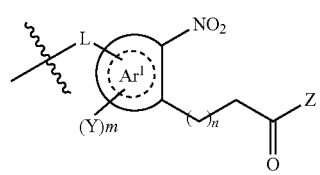
III where Ar$^1$, m, n, Y, and L are those defined herein and Z is selected from the group consisting of 5-fluorouridine, 5-fluorouracil, and a prodrug thereof, provided at least one R moiety is of Formula III.

Another aspect of the invention provides a nitroreductase-releasable pro-drug of the formula:

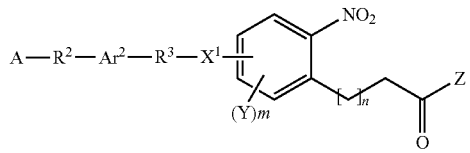

where m is an integer from 0 to 3; n is 0 or 1; Z is a pharmaceutically active compound or a pro-drug thereof, Y is halide, alkyl, alkoxy, acetoxy, phenyl, or —N═N-Phenyl; X$^1$ is O, S, or NR$^1$, wherein R$^1$ is hydrogen, alkyl, aryl, aralkyl, heteroalkyl, cycloalkyl, cycloalkylalkyl, or oxygen; Ar$^2$ is heteroaryl; each of R$^2$ and R$^3$ is independently C$_1$-C$_{20}$ alkylene or C$_1$-C$_{20}$ heteroalkylene; and A is a monosaccharide, a disaccharide, or a carbocyclic sugar.

In some embodiments, m is 0.

Still in other embodiments, each of R$^2$ and R$^3$ is independently selected from the group consisting of C$_1$-C$_8$ alkylene and —[OCH$_2$CH$_2$]$_a$—, wherein a is an integer from 1 to 5.

Yet in other embodiments, A is selected from the group consisting of allose, altrose, glucose, mannose, gulose, idose, galactose, talose, ribose, arabinose, xylose, lyxose, psicose, fructose, sorbose, tagatose, ribulose, xylulose, myo-inositol, scyllo-inositol, muco-inositol, D-chiro-inositol, neo-inositol, L-chiro-inositol, allo-inositol, epi-inositol, cis-inositol, sucrose, lactose, maltose, trehalose, cellobiose, lactulose, and chitobiose.

In further embodiments, Z is selected from the group consisting of 3-indolepropionic acid, 5-aminosalicylic acid, acetylsalicylic acid, budesonide, celecoxib, 5-fluorouracil, folinic acid, irinotecan, metformin, metronidazole, prednisolone, regorafenib, salicylic acid, 2'-deoxy-5-fluorouridine, and a derivative thereof.

In one particular embodiment, Ar$^2$ is 1H-1,2,3-triazolyl.

DETAILED DESCRIPTION OF THE INVENTION

The role of nitroreductases produced by gut flora in the reduction of nitroaromatic compounds was established in 1973. Two families of nitroreductase enzymes have been discovered. Type I nitroreductases are oxygen-insensitive and catalyze three sequential transfers of two electrons from NADP(H) to nitro groups present on aromatic or heteroaromatic rings, producing in turn the corresponding nitroso, hydroxylamine, and amine compounds. Type I nitroreductases are produced by many anaerobic bacteria living in the distal human gut and generally exhibit broad substrate profiles. Nitro group reductions by nitroreductases have been employed to activate pro-drugs as drugs and to release drugs from pro-drugs by a cascade cyclization as generalized in Scheme 1.

Scheme 1

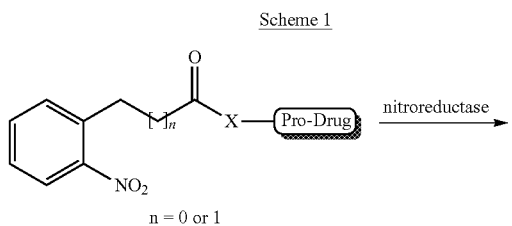

n = 0 or 1

-continued

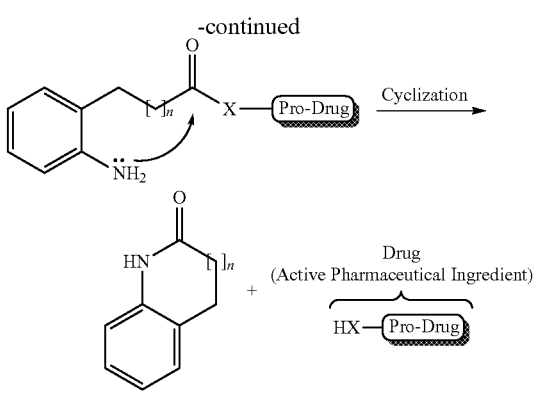

As can be seen in Scheme 1, the drug or the active pharmaceutical ingredient includes "HX—" moiety resulting from the cleavage via cyclization of the molecule. In a similar manner, it should be appreciated that in some embodiments for compounds of the invention, the drug or the active pharmaceutical ingredient that is released from the pro-drug is of the formula "H—Z". In other embodiments, the released compound H—Z itself can be a pro-drug.

Some aspects of the invention are based at least in part on utilizing the presence of nitroreductase in the distal gut of a subject to release and deliver an active pharmaceutical ingredient or a prod-drug thereof (e.g., a drug such as 5-fluorouracil or 5-FU or its prodrug such as 5-fluorouridine) to the colon. Compounds of the invention can be used to deliver drugs specifically to the gastrointestinal (GI) tract. In some embodiments, it is believed that at least about 80%, typically at least about 90%, often at least 95%, and most often at least about 98% of Z is delivered to the distal gut region of the subject.

Surprisingly and unexpectedly, the present inventors have discovered that a nitroreductase-releasable pro-drug of the formula:

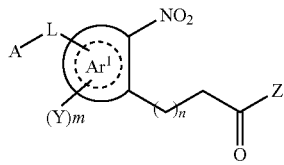

I can be used to orally deliver various active pharmaceutical ingredients to the GI tract of a subject, in particular to the distal gut region of the subject. By using a prodrug of Formula I, it was discovered that the bioavailability and/or half-life of the pharmaceutically active compound in the GI tract region can be significantly increased. More significantly, use of a prodrug compound of Formula I significantly reduces systemic release of the active pharmaceutical ingredient. By reducing the amount of systemic release of an active pharmaceutically ingredient, one can significantly reduce the side-effects of the pharmaceutically active compound, increase the drug's effective delivery dosage, improve oral bioavailability, and/or increase the half-life of the pharmaceutically active compound. In compounds of Formula I. $Ar^1$ is aryl or heteroaryl; m is an integer from 0 to (t−3), wherein t is a total number of substituents possible on $Ar^1$; n is 0 or 1; Z is a pharmaceutically active compound or a prodrug thereof; Y is halide, alkyl, alkoxy, acetoxy, phenyl, or —N=N-Phenyl; L is a linker; and A is a carbohydrate or a derivative thereof. As used herein "a derivative of carbohydrate" refers to a carbohydrate in which one or more hydroxyl group is replaced with hydrogen (e.g., 2-deoxy carbohydrate), or halide (e.g., 2-fluoro carbohydrate), or one or more hydroxyl groups are protected (e.g., with acetyl, methyl, ethyl, or in the form of an acetonide protecting group).

The term "sugar" and "carbohydrate" are used interchangeably herein and includes carbocyclic sugars such as inositol or myo-inositol, and its isomers, e.g., scyllo-inositol, muco-inositol, D-chiro-inositol, neo-inositol, L-chiro-inositol, allo-inositol, epi-inositol, and cis-inositol. Sugar can be a monosaccharide, disaccharide, or higher oligosaccharide. Typically, the carbohydrate of the invention is a monosaccharide, disaccharide, trisaccharide, or a carbocyclic sugar. As used herein, the term "derivative" refers to a derivative of a sugar in which one or more of the hydroxyl groups is replaced with hydrogen (e.g., 2-deoxyglucose, 2-deoxyinositol, 5-deoxyglucose, etc.), an amine (e.g., amino sugars), or is replaced with a halogen, such as chloro, fluoro, or iodo, (e.g., 5-fluoroglucose, 2-fluoroglucose, 5-chloroglucose, 2-chloroglucose, etc.). Sugar can be an (L)-isomer or a (D)-isomer.

The term "monosaccharide" refers to any type of hexose of the formula $C_6H_{12}O_6$ or a derivative thereof as well as pentose carbohydrates and derivatives thereof that are known to one skilled in the art (e.g., ribose, etc.). The ring structure (i.e., ring type) of the monosaccharide can be a pyranose, a furanose, or in case of a carbocyclic sugar a cyclohexane. In addition, the monosaccharides of a pyranose or a furanose form can be an α- or β-anomer. Monosaccharide can be a ketonic monosaccharide (i.e., ketose), an aldehyde monosaccharide (i.e., aldose), carbocyclic, or any type of hexose of the formula $C_6H_{12}O_6$ or a derivative thereof. Exemplary aldoses of the invention include, but are not limited to, allose, altrose, glucose, mannose, gulose, idose, galactose, talose, ribose, arabinose, xylose, lyxose, and derivatives thereof. Exemplary ketoses of the invention include, but are not limited to, psicose, fructose, sorbose, tagatose, ribulose, xylulose, and derivatives thereof. Exemplary carbocyclic sugars include myo-inositol, scyllo-inositol, muco-inositol, D-chiro-inositol, neo-inositol, L-chiro-inositol, allo-inositol, epi-inositol, and cis-inositol.

The term "disaccharide" refers to a carbohydrate composed of two monosaccharides. It is formed when two monosaccharides are covalently linked to form a dimer. The linkage can be a (1→4) bond, a (1→6) bond, a (1→2) bond, etc. between the two monosaccharides. In addition, each of the monosaccharides can be independently an α- or β-anomer. Exemplary disaccharides that can be used in the present invention include, but are not limited to, sucrose, lactose, maltose, trehalose, cellobiose, lactulose, and chitobiose, etc. Each of the component monosaccharides can independently be a ketonic monosaccharide (i.e., ketose), an aldehyde monosaccharide (i.e., aldose), or any type of hexose of the formula $C_6H_{12}O_6$ or a derivative thereof. Exemplary aldoses that can be used in preparing disaccharides of the invention include, but are not limited to, allose, altrose, glucose, mannose, gulose, idose, galactose, talose, ribose, arabinose, xylose, lyxose, and derivatives thereof. Exemplary ketoses that can be used in preparing disaccharides of the invention include, but are not limited to, psicose, fructose, sorbose, tagatose, ribulose, xylulose, and derivatives thereof. Each monosaccharide can also be independently an (L)-isomer or a (D)-isomer.

Exemplary sugars or carbohydrates of the invention include, but are not limited to, the following chemical formulas:

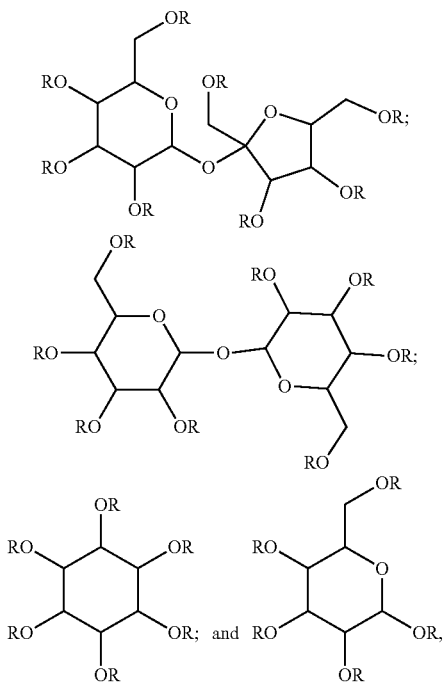

where each R is as defined herein. It should be appreciated that each chiral center in the carbohydrates of the invention can be of either the (R) or (S) configuration.

Some specific isomeric carbohydrates of the invention include, but are not limited to, the following carbohydrates:

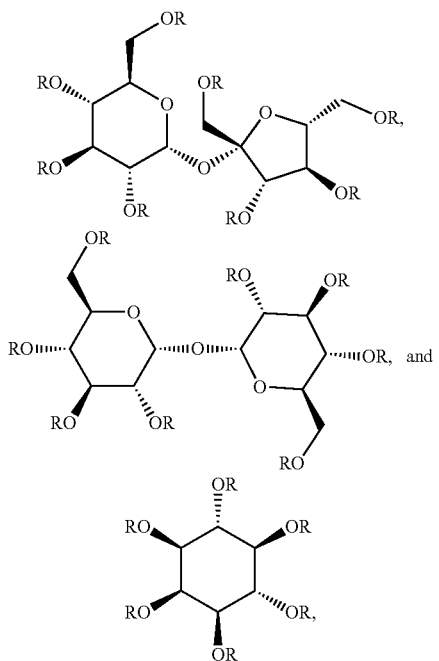

where each R is as defined herein.

As stated throughout this specification, the scope of the invention is not limited to these particular isomers. As will be readily recognized, the scope of the invention includes all variations of the isomers of carbohydrates disclosed above.

"Alkyl" refers to a saturated linear monovalent hydrocarbon moiety of one to twenty, typically one to twelve, often one to ten, and more often one to six carbon atoms or a saturated branched monovalent hydrocarbon moiety of three to twenty, typically three to twelve, often three to ten, and more often three to six carbon atoms. In some instances, one or more hydrogen atom of the alkyl group can be replaced with a halide such as chloride, fluoride, bromide, or iodide. Exemplary alkyl groups include, but are not limited to, methyl, ethyl, n-propyl, 2-propyl, tert-butyl, pentyl, trifluoromethyl, fluoromethyl, and the like.

"Alkylene" refers to a saturated linear divalent alkyl group. Exemplary alkylene groups include, but are not limited to, methylene, ethylene, propylene, difluoromethylene, tetrafluoroethylene, butylene, pentylene, and the like.

"Aryl" refers to a mono-, bi-, or tricyclic aromatic hydrocarbon moiety of 6 to 15 ring atoms which is optionally substituted with one or more substituents within the ring structure. Exemplary aryl groups include, but are not limited to, phenyl, 1-naphthyl, 2-naphthyl, anthracenyl, phenanthrenyl, and the like.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

The terms "halo," "halogen," and "halide" are used interchangeably herein and refer to fluoro, chloro, bromo, or iodo.

The term "heteroalkyl" refers to a branched or unbranched, cyclic or acyclic saturated alkyl moiety containing carbon, hydrogen and one or more heteroatoms in place of a carbon atom, or optionally one or more heteroatom-containing substituents independently selected from =O, —OR$^a$, —C(O)R$^a$, —NR$^b$R$^c$, —C(O)NR$^b$R$^c$ and —S(O)$_n$R$^d$ (where n is an integer from 0 to 2). R$^a$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. R$^b$ is hydrogen, alkyl, haloalkyl, cycloalkyl, cycloalkylalkyl, heterocyclyl, heterocyclylalkyl, aryl, aralkyl, heteroaryl, heteroaralkyl, or acyl. R$^c$ is hydrogen, alkyl, haloalkyl, cycloalkyl, cycloalkylalkyl, heterocyclyl, heterocyclylalkyl, aryl, aralkyl, acyl, alkylsulfonyl, carboxamido, or mono- or di-alkylcarbomoyl. Optionally, R$^b$ and R$^c$ can be combined together with the nitrogen to which each is attached to form a four-, five-, six- or seven-membered heterocyclic ring (e.g., a pyrrolidinyl, piperidinyl or morpholinyl ring). R$^d$ is hydrogen (provided that n is 0), alkyl, haloalkyl, cycloalkyl, cycloalkylalkyl, heterocyclyl, heterocyclylalkyl, aryl, aralkyl, heteroaryl, heteroaralkyl, acyl, amino, monosubstituted amino, disubstituted amino, or hydroxyalkyl. Representative examples include, for example, 2-methoxyethyl, benzyloxymethyl, thiophen-2-yl-thiomethyl, 2-hydroxyethyl, and 2,3-dihydroxypropyl. In one particular embodiment, "heteroalkyl" refers to a chain of atoms having $C_{1-20}$, $C_{2-20}$, often $C_{2-12}$, more often $C_{2-8}$, and most often $C_{2-6}$ carbon atoms with addition 1-5 heteroatoms (e.g., O, S, N) in the chain provided no two oxygen atoms are linked to each other. Exemplary heteroalkyls include oligomers of ethylene glycol, propylene glycol, etc. In one particular embodiment, heteroalkyl is a moiety of the formula —[OCH$_2$CH$_2$]$_a$—, wherein a is an integer from 1 to 5.

"Pharmaceutically acceptable excipient" refers to an excipient that is useful in preparing a pharmaceutical composition that is generally safe, non-toxic and neither biologically nor otherwise undesirable, and includes an excipient that is acceptable for veterinary use as well as for human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-lcarboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug in vivo when such prodrug is administered to a mammalian subject. Typically, a prodrug is one in which a functional group of the drug is in the form of a protecting group, such as with an acetyl group or other esters, an alkyl group, or an ether group, etc.

"Protecting group" refers to a moiety, except alkyl groups, that, when attached to a reactive group in a molecule, masks, reduces, or prevents that reactivity. Examples of protecting groups can be found in T. W. Greene and P. G. M. Wuts, *Protective Groups in Organic Synthesis*, 3rd edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethylsilyl (TMS), 2-trimethylsilylethanesulfonyl (SES), trityl and substituted trityl groups, allyloxycarbonyl, 9-fluorenylmethyloxycarbonyl (FMOC), nitroveratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity, and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As used herein, the term "treating", "contacting," or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

As used herein, the terms "those defined above," and "those defined herein" when referring to a variable incorporates by reference the broad definition of the variable as well as preferred, more preferred and most preferred definitions, if any.

The term "heteroaryl" refers to a monocyclic or bicyclic aromatic moiety of 5 to 20 ring atoms containing from one to five, typically one to three, ring heteroatoms selected from N, O, or S, the remaining ring atoms being C. The heteroaryl ring can optionally substituted independently with one or more substituents. Exemplary heteroaryls include, but are not limited to, pyridinyl, furanyl, thiophenyl, thiazolyl, isothiazolyl, triazolyl, triazinyl, imidazolyl, oxazolyl, isoxazolyl, pyrrolyl, pyrazolyl, pyrazinyl, pyrimidinyl, benzofuranyl, isobenzofuranyl, benzothiazolyl, benzoisothiazolyl, benzotriazolyl, indolyl, isoindolyl, benzoxazolyl, thiazolyl, isothiazolyl, quinolyl, isoquinolyl, benzimidazolyl, benzisoxazolyl, benzothiophenyl, dibenzofuran, and benzodiazepin-2-one-5-yl, and the like.

The term "about" or "approximately" as used herein in reference to a particular numerical value refers to being within an acceptable error range for the particular value as determined by one of ordinary skill in the art, which will depend in part on how the value is measured or determined, i.e., the limitations of the measurement system, i.e., the degree of precision required for a particular purpose. For example, the term "about" can mean within 1 or more, typically one standard deviation, per the practice in the art. Alternatively, the term "about" when referring to a numerical value can mean±20%, typically ±10%, often ±5% and more often ±1% of the numerical value. In general, however, where particular values are described in the application and claims, unless otherwise stated, the term "about" means within an acceptable error range for the particular value.

Without being bound by any theory, it is believed that compounds of the present invention allow delivery of an active pharmaceutical ingredient to the distal gut region, e.g., colon and/or rectum, of the subject when administered orally. In this manner, any clinical condition associated with the distal gut region can be treated by using an appropriate drug that is attached to the delivery vehicle of the invention. In particular, the delivery vehicle refers to a moiety of the formula:

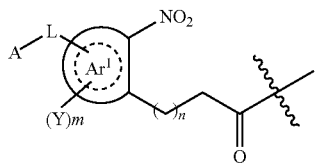

where A, L, Ar¹, Y, m, and n are those defined herein. Thus, moiety V in essence serves as a pro-drug moiety portion for delivering the active pharmaceutical ingredient H—Z, where Z is as defined herein.

In one particular embodiment, linkers L are those disclosed in the commonly assigned U.S. patent application Ser. No. 15/233,907, filed Aug. 10, 2016, which is incorporated herein by reference in its entirety. Other suitable linkers include polyethylene glycol (e.g., having 2-20, typically 2-15, and often 2-10 ethylene glycol moieties), as well as a mixture of one or more of a straight chain, a branched, and/or a cyclic hydrocarbon optionally having one or more heteroatoms. Thus, the linker can include alkyl chains having one or more cycloalkyl, heterocycloalkyl, heteroaryl, or aryl within the overall chain length. In some embodiments, the linker is a polyethylene glycol linker of the formula —(CH$_2$)$_2$—[O—(CH$_2$)$_2$]$_n$—, where n is an integer from 1 to about 20, typically from 1 to about 15 and often from 1 to about 10.

In some embodiments, by attaching to the delivery vehicle V the amount of drug that passes through the stomach and into the distal gut region (i.e., the amount of drug delivered to the distal gut region) is at least about 80%, typically at least about 90%, and often at least about 95%. Alternatively, the amount of systemic release of the active pharmaceutical ingredient is reduced by at least about 30%, typically by at least about 50%, often by at least 70%, more often by at least 80%, and most often by at least 90%, compared to oral administration of the active pharmaceutical ingredient or a salt thereof, i.e., in the absence of the delivery vehicle of formula V.

The active pharmaceutical ingredient Z depends on the type of clinical conditions to be treated. Exemplary clinical conditions that occur in distal gut region of a subject include colorectal cancer, inflammatory bowel disease (IBD), infectious diarrhea, bacterial infections, and bacterial overgrowth. Some of the representative active pharmaceutical ingredients that can be attached to the delivery vehicle V include, but are not limited to, 3-indolepropionic acid, 5-aminosalicylic acid, acetylsalicylic acid, budesonide, celecoxib, 5-fluorouracil, folinic acid, irinotecan, metformin, metronidazole, prednisolone, regorafenib, salicylic acid, and the like. In general, any drug that can be attached as an ester or an amide to the delivery vehicle V can be used. As will be recognized, in order to form an ester or an amide with the delivery vehicle V, the drug to be delivered to the distal gut region should have a hydroxyl, a thiol, or an amine functional group, which can be used to covalently link to the delivery vehicle V. The delivery vehicle V protects the drug from the environment of the upper gastrointestinal (GI) tract. It is substantially inert to stomach acid, enzymes in the upper GI tract, and absorption in the small intestine. As such, the use of the delivery vehicle V allows at least about 80%, typically at least about 85%, often at least about 90%, and more often 95% of the drug to be delivered to the distal gut region (e.g., colon and/or rectum), affording better dosage control and greater clinical efficacy in oral administration of the drug. It should be appreciated that the active pharmaceutical ingredient referred to herein in this paragraph refers to the active pharmaceutical ingredient that is released by cleavage from the delivery vehicle V.

Moreover, a solid pharmaceutical composition (e.g., tablets, capsules, pills, etc.) comprising a nitroreductase-releasable compound of formula I can be made smaller, since this pro-drug does not need protective coatings. In addition, compounds of formula I can be taken in the form of a flavored syrup, or it can be incorporated into foods, like yoghurt or frozen popsicles, to make it even more palatable. These improvements in pro-drug formulation will result in greater patient compliance and better control of clinical conditions associated with the distal gut region, such as IBD, colorectal cancer, infectious diarrhea, bacterial infections, and bacterial overgrowth, etc.

While compounds of the present invention can be used to treat a variety of clinical conditions associated with distal gut region using an appropriate drug as described above, for the sake of brevity and clarity, the present invention will now be described in further detail with reference to treating colorectal cancer with 5-fluorouracil. However, it should be appreciated that the scope of the present invention includes treating other clinical conditions using an appropriate drug as disclosed above.

Treatment of colorectal cancer can include primary, adjuvant, and neoadjuvant chemotherapy using a compound of formula I, where Z can incorporate 5-fluorouracil, such as a moiety of formula IVA or IVB. The 5-fluorouracil pro-drug 3 (see Scheme) can be prepared as described in the Examples section. Following oral administration, a compound of formula I survives to reach the distal gut region, where the nitro group of 3 is reduced by nitroreductase enzymes to produce amine compound 4. An intramolecular cyclization then releases 5-fluorouracil (via the prodrug 3-O-acetyl-5-fluorouridine). The resulting derivative of the carrier scaffold, 5, is then excreted with feces.

Scheme 2

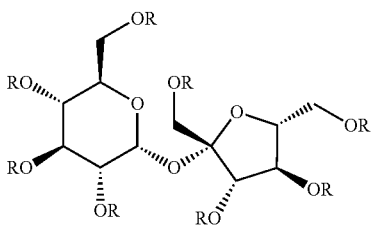

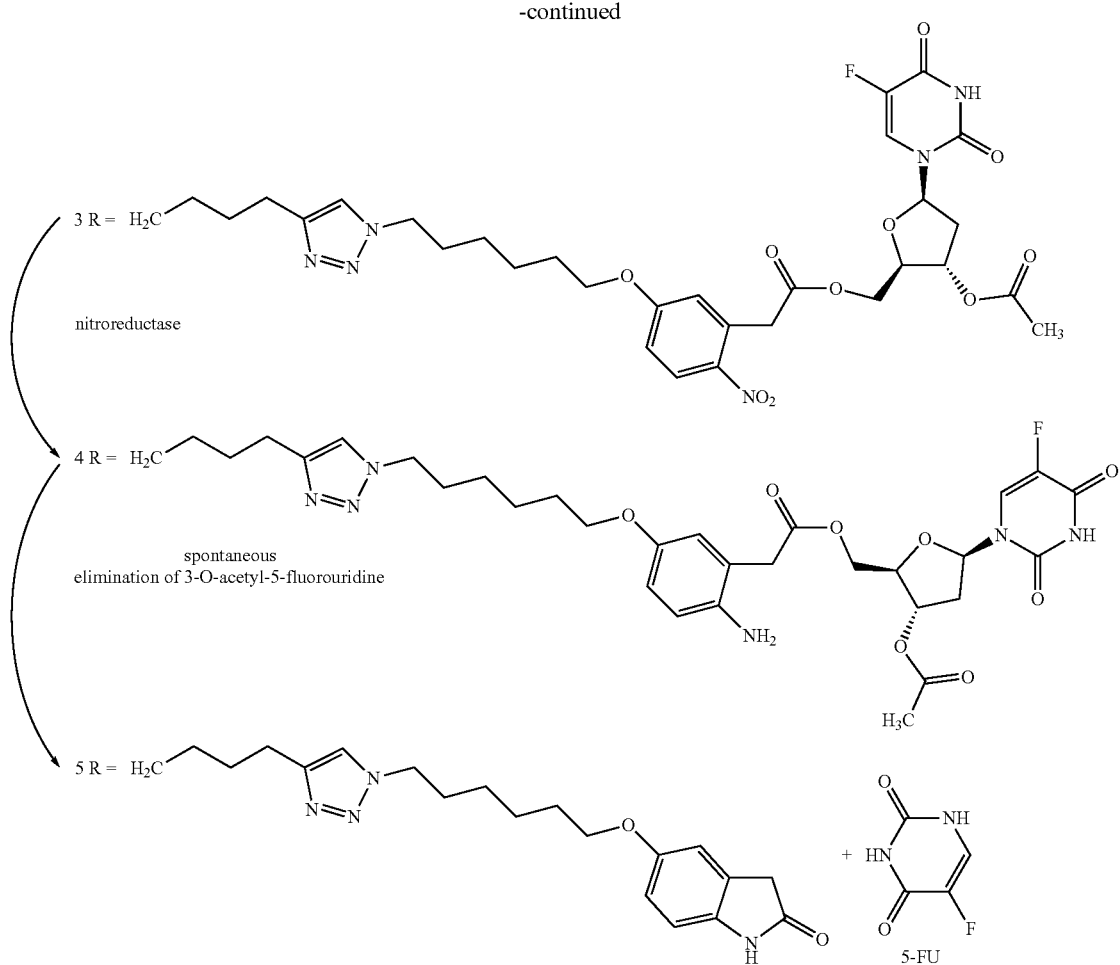

With regard to compounds of formula I, moiety A (carbohydrate) can be any carbohydrate described above. It should be noted that when m is 0, it means no substituent (other than hydrogen) is present in Ar¹. When n is 0, the resulting amide (e.g., far right portion of compound 5 in Scheme 2) is contained in a five-membered ring, and similarly, when n is 1, the resulting amide of compound 5 is contained in a six-membered ring. Suitable substituent(s) Y in compounds of formula I include halide, such as fluoride, chloride, bromide, or iodide. In some embodiments, when Y is present, each Y is independently fluoride or chloride.

Referring again to compounds of formula I, suitable Ar¹ include, but are not limited to, benzene (i.e., phenyl moiety), anthracene, phenanthrene, azobenzene, and heteroaryl such as pyridine. In one particular embodiment, Ar¹ is benzene (i.e., phenyl).

In one particular embodiment, L is a moiety of the formula:

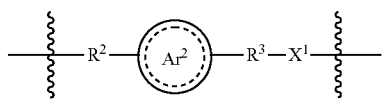

II where Ar² is aryl or heteroaryl; each of $R^2$ and $R^3$ is independently alkylene; and $X^1$ is O, S, or $NR^1$, wherein $R^1$ is hydrogen, alkyl, aryl, aralkyl, heteroalkyl, cycloalkyl, cycloalkylalkyl, or oxygen.

The term "aralkyl" means a moiety —$R^a R^b$ where $R^a$ is an alkylene group and $R^b$ is an aryl group as defined above, e.g., benzyl, phenylethyl, 3-(3-chlorophenyl)-2-methylpentyl, and the like. The term "cycloalkyl" refers to a saturated monovalent cyclic hydrocarbon moiety of three to seven ring carbons. The cycloalkyl may be optionally substituted independently with one, two, or three substituents selected from alkyl, haloalkyl, halo, nitro, cyano, heteroalkyl, optionally substituted phenyl, optionally substituted heteroaralkyl, or —C(O)R (where R is hydrogen, alkyl, haloalkyl, amino, monosubstituted amino, disubstituted amino, hydroxy, alkoxy, or optionally substituted phenyl). More specifically, the term cycloalkyl includes, for example, cyclopropyl, cyclohexyl, 1,2-dihydroxycyclopropyl, and the like. The term "cycloalkylalkyl" means a moiety —$R^a R^b$ where $R^a$ is an alkylene group and $R^b$ is a cycloalkyl group as defined herein. Exemplary cycloalkylalkyl includes, cyclopropylmethyl, cyclohexylpropyl, 3-cyclohexyl-2-methylpropyl, and the like.

In one specific embodiment, Ar² is a triazole. $R^2$ and $R^3$ are independently selected from the group consisting of $C_1$-$C_5$ alkylene and —[OCH₂CH₂]$_a$—, wherein a is an integer from 1 to 5. For example, $R^2$ or $R^3$ can be formed from an ethylene glycol derivative such that $R^2$ or $R^3$ includes a moiety of the formula: —O—(CH$_2$)$_2$—O—; —(CH$_2$)$_2$—O—; or —O—(CH$_2$)$_2$—. Typically, $R^2$ or $R^3$ has one to six chain atoms, where each chain atom is independently C, O, N, or S, provided the chain meets the requirement described in this paragraph. In one specific embodiment, $R^2$ is propylenyl.

Yet in other embodiments, $R^3$ has two to ten chain atoms, where each chain atom is independently C, O, N, or S, provided the chain meets the requirement described in this paragraph. In one specific embodiment, $R^3$ is —(CH$_2$)$_6$—O—. In other embodiments, $R^3$ is selected from the group consisting of: —(CH$_2$)$_x$—O—, where x is an integer from 2 to 12, typically from 2 to 10, often 2 to 8, and more often 2 to 6; and —(CH$_2$)$_2$—O—(CH$_2$)$_2$—O—.

Still further, combinations of the various groups described herein form other particular embodiments. For example, in one particularly preferred embodiment Ar$^1$ is phenyl, n is 0 or 1, m is 0, Z is a moiety of formula A or B, A is a moiety of the formula:

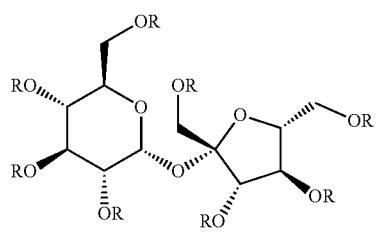

and L is a moiety of the formula: —(CH$_2$)$_3$-(Triazole)-(CH$_2$)$_6$—O—. In this manner, a wide variety of compounds of formula I are embodied within the present invention. For example, some of the representative compounds of the invention include, but are not limited to, the following combination of moieties:

A1
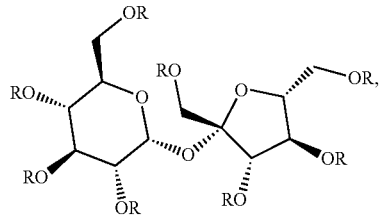

A2
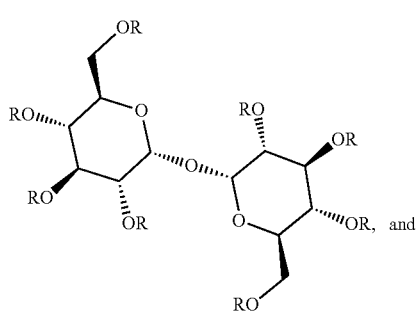

A3
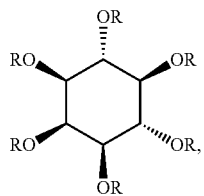

where for each A-1, A-2, and A-3, R is:

B1
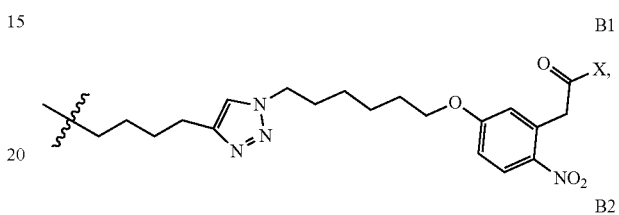

B2
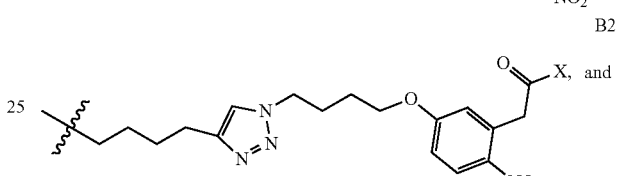

B3
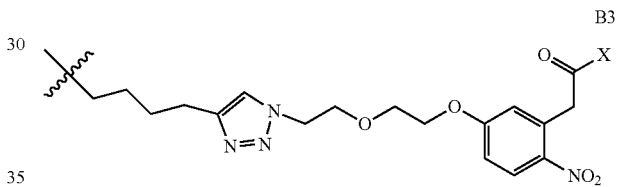

and where

C1
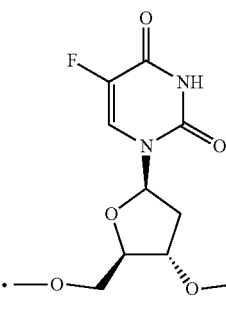

C2
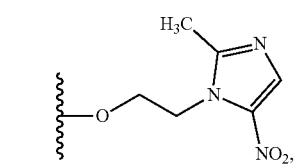

C3
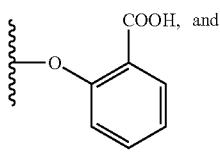

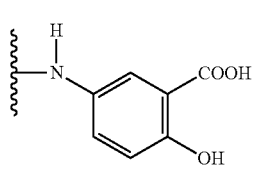

C4

More specific representative compounds of the invention include, but not limited to, the compounds with the following combination of moieties: A1 with B1, and C1-C4; A1 with B2, and C1-C4; A1 with B3, and C1-C4; A2 with B1, and C1-C4; A2 with B2, and C1-C4; ... A3 with B1, and C1-C4; A3 with B2, and C1-C4; and A3 with B3, and C1-C4.

Administration

The compounds of the present invention can be administered to a patient or a subject to achieve a desired physiological effect. While the compound can be administered in a variety of forms adapted to the chosen route of administration, i.e., orally or parenterally, the compound of the invention is particularly suited for oral administration or alternatively it can be administered as a suppository to the rectal system.

The compound of the invention is typically administered orally, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Such compositions and preparation can contain at least 0.1% of the compound of formula I. The percentage of the compositions and preparation can, of course, be varied and can conveniently be between about 1 to about 10% of the weight of the unit. The amount of compound of formula I in such therapeutically useful compositions is such that a suitable dosage will be obtained. Preferred compositions or preparations according to the present invention are prepared such that an oral dosage unit form contains from about 1 to about 1000 mg of compound of formula I.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens preservatives, a dye and flavoring such as cherry or orange flavor. Of course, any material used in preparing any dosage unit form should be pharmaceutically pure and substantially non-toxic in the amounts employed. In addition, compounds of formula I can be incorporated into sustained-release preparations and formulations.

Compounds of formula I can be administered to a mammal alone or in combination with pharmaceutically acceptable carriers, as noted above, the proportion of which is determined by the solubility and chemical nature of the compound and standard pharmaceutical practice.

The physician will determine the dosage of the present therapeutic agents which will be most suitable for treatment and it will vary with the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

A pro-drug of 5-fluorouracil of formula I is prepared as follows:

Scheme 3

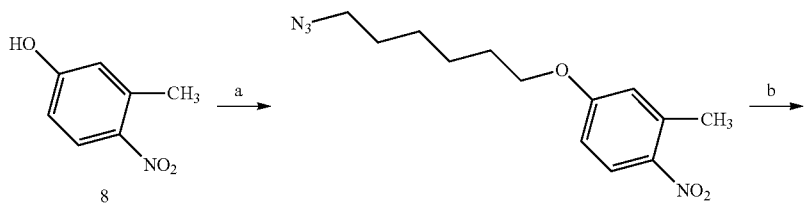

-continued
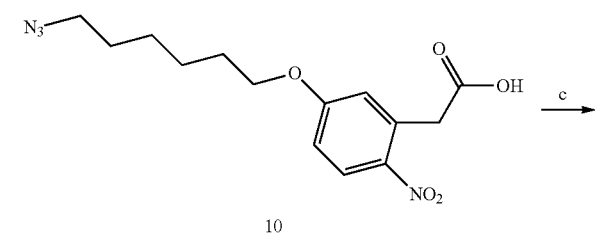
10
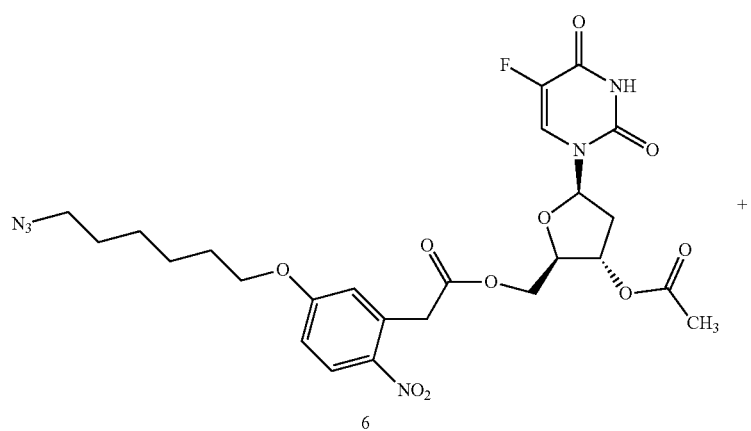
6
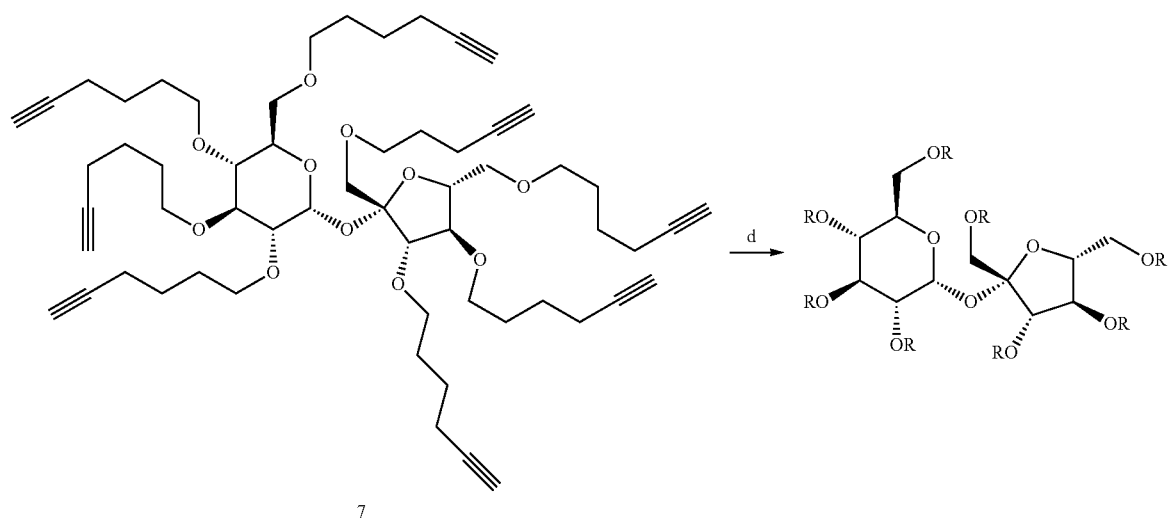
7
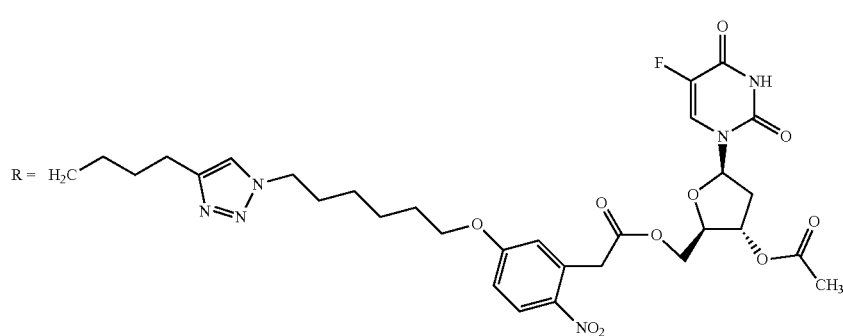
3
REAGENTS: (a) N₃(CH₂)₆Br, K₂CO₃, acetone, RT. (b) 1. NaOCH₂CH₃, CH₃CH₂OH; diethyl oxalate. 2. 30% H₂O₂. (c) 1. SOCl₂. 2. 1-acetyl-5-fluorouracil, (CH₃CH₂)₃N, 1,4-dioxane. 3. CH₃CH₂OH. (d) CuSO₄, sodium ascorbate, THF/water.

3-O-acetyl-5-fluorouridine prodrug 3 is prepared by means of a copper-catalyzed azide-alkyne cycloaddition (CuAAC) reaction (see Scheme 3). This process was used to prepare other compounds of Formula I in high chemical yields. Preparation of azide 6 is also shown in Scheme 3. Briefly, commercially available 3-methyl-4-nitrophenol (8) was O-alkylated using 1-azido-6-bromohexane to produce compound 9. Acylation of 9 with diethyl oxalate, followed by oxidative cleavage with hydrogen peroxide, afforded acid 10. Conversion of 10 to the corresponding acid chloride using thionyl chloride, followed by acylation at O of 3-O-acetyl-5-fluorouridine affords azide 6. It should be appreciated that azide 6 can be prepared using other methods, which are well known to one skilled in the art given the present disclosure. Preparation of the required octaalkyne 7 from sucrose has previously been published by the present inventors. See, for example, *ACS Med. Chem. Lett.* (2012) 3, 710-714. Reaction of compound 7 with an excess of azide 6 under standard CuAAC conditions provides the 3-O-acetyl-5-fluorouridine prodrug 3, which is purified using methods well known to one skilled in the art (e.g., recrystallization, chromatography, HPLC, LPLC, etc.) and characterized using, for example, mass spectrometry, nuclear magnetic resonance (e.g., $^1$H and $^{13}$C NMR), infrared spectroscopy, and UV/VIS spectroscopy.

Synthesis of Prodrug Compounds:

A mixture of 3-methyl-4-nitrophenol (1, 12.3 g, 80.3 mmol), 1,6-dibromohexane (30 mL, 47.6 g, 195 mmol), and finely ground anhydrous potassium carbonate (40 g, 289 mmol) in anhydrous DMF (250 mL) was rapidly stirred at room temperature under argon for 16 hr. The mixture was then diluted with water (700 mL), extracted with $CH_2Cl_2$ (3×250 mL), the extracts washed with water (500 mL), dried over anhydrous $Na_2SO_4$, filtered, and volatiles removed in vacuo. The residue (50 g) was chromatographed on silica gel 60 (200 g) eluted with 10% EtOAc/hexanes to remove DMF. The recovered crude product was chromatographed on silica gel 60 (250 g) eluted with hexanes to remove 1,6-dibromohexane. The recovered crude product was chromatographed on silica gel 60 (250 g) eluted with 10% EtOAc/hexanes, affording the product 2 as an oil ($R_f$ 0.25, 10% EtOAc/heptane) that slowly crystallized. Yield 19.8 g (62.6 mmol, 78%).

A mixture of compound 2 (16.3 g, 51.6 mmol) and sodium azide (6.5 g, 100 mmol) in anhydrous DMSO (100 mL) was rapidly stirred at room temperature under argon for 16 hr. The mixture was then diluted with water (1 L), extracted with ether (3×200 mL), the extracts washed with 50% saturated NaCl solution (300 mL), dried over anhydrous $MgSO_4$, filtered, and volatiles removed in vacuo. Product 3 was obtained as an oil homogeneous by TLC ($R_f$ 0.55, 40% EtOAc/heptane). Yield 14.3 g (51.4 mmol, 99%).

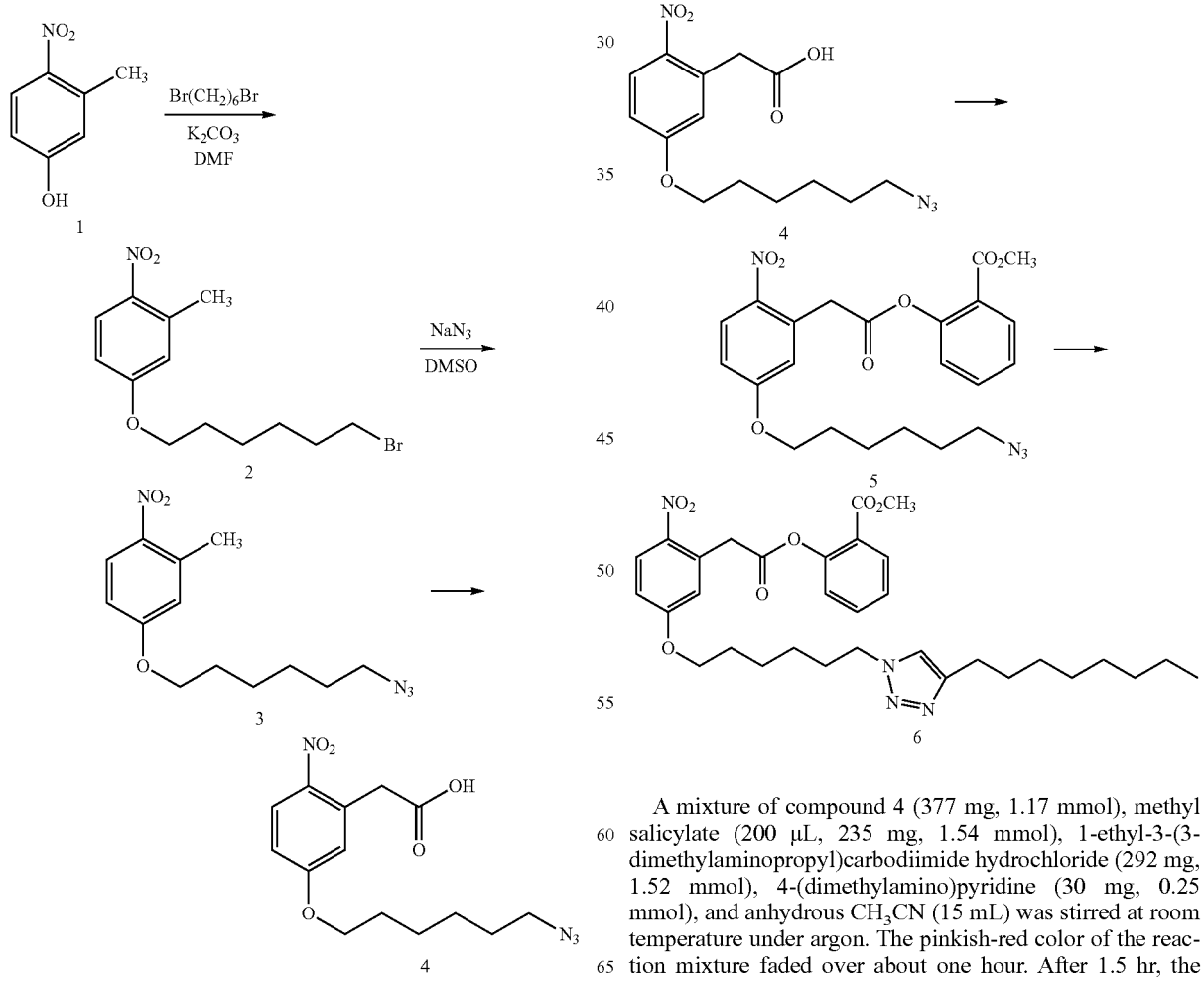

A mixture of compound 4 (377 mg, 1.17 mmol), methyl salicylate (200 µL, 235 mg, 1.54 mmol), 1-ethyl-3-(3-dimethylaminopropyl)carbodiimide hydrochloride (292 mg, 1.52 mmol), 4-(dimethylamino)pyridine (30 mg, 0.25 mmol), and anhydrous $CH_3CN$ (15 mL) was stirred at room temperature under argon. The pinkish-red color of the reaction mixture faded over about one hour. After 1.5 hr, the mixture was diluted with 50% saturated $NaHCO_3$ solution (150 mL), extracted with $CH_2Cl_2$ (3×100 mL), the extracts washed with 50% saturated NaCl solution (150 mL), dried over anhydrous Na₂SO₄, filtered, and volatiles removed in vacuo. The residue was chromatographed on silica gel 60 (100 g) eluted with 25% EtOAc/hexanes, affording the product 5 as an oil homogeneous by TLC(R$_f$ 0.24, 30% EtOAc/heptane). Yield 410 mg (0.90 mmol, 77%).

To a mixture of compound 5 (410 mg, 0.90 mmol) and 1-decyne (300 μL, 230 mg, 1.66 mmol) in THF (25 mL) and water (1 mL) that had been deoxygenated for 15 min using a stream of argon were added with vigorous stirring at room temperature anhydrous cupric sulfate (130 mg, 0.81 mmol) and sodium ascorbate (270 mg, 1.38 mmol). The mixture was stirred under argon for 16 hr. Silica gel 60 (~5 g) was added to the mixture and volatiles were removed in vacuo. The silica gel was applied to the top of a silica gel 60 column (100 g) and the column eluted with 60% EtOAc/hexanes. Product 6 was obtained as a pale yellow oil homogeneous by TLC (R$_f$ 0.27, 60% EtOAc/heptane). Yield 459 mg (0.77 mmol, 86%).

and volatiles removed in vacuo. The residue was chromatographed on silica gel 60 (100 g) eluted with 75% EtOAc/hexanes, affording the product 7 as a pale yellow oil homogeneous by TLC(R$_f$ 0.27, 80% EtOAc/heptane). Yield 470 mg (1.0 mmol, 82%).

To a mixture of compound 7 (470 mg, 1.0 mmol) and 1-decyne (300 μL, 230 mg, 1.66 mmol) in THF (25 mL) and water (1 mL) that had been deoxygenated for 15 min using a stream of argon were added with vigorous stirring at room temperature anhydrous cupric sulfate (120 mg, 0.75 mmol) and sodium ascorbate (240 mg, 1.22 mmol). The mixture was stirred under argon for 16 hr. Silica gel 60 (~5 g) was added to the mixture and volatiles were removed in vacuo. The silica gel was applied to the top of a silica gel 60 column (50 g) and the column eluted with EtOAc. Product 8 was obtained as a pale yellow oil homogeneous by TLC (R$_f$ 0.14, EtOAc). Yield 450 mg (0.73 mmol, 73%).

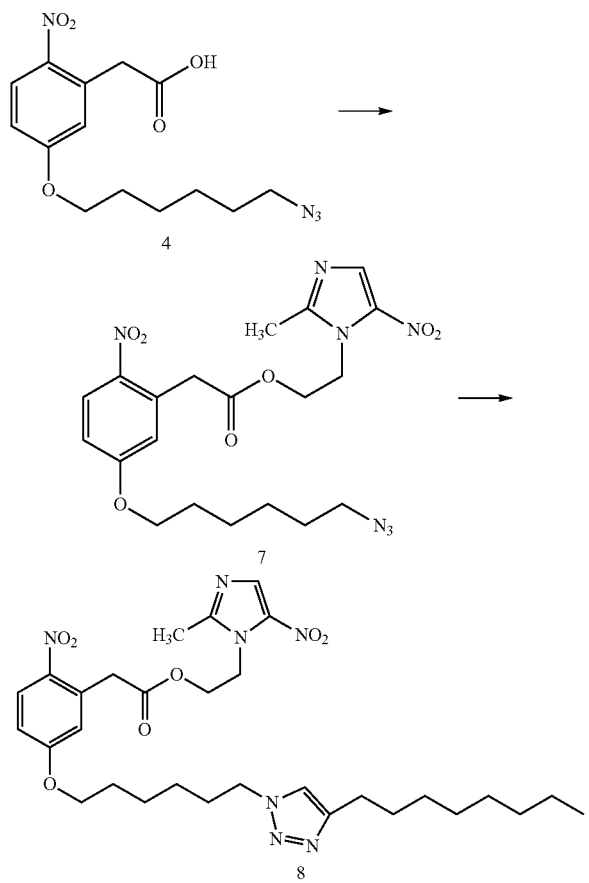

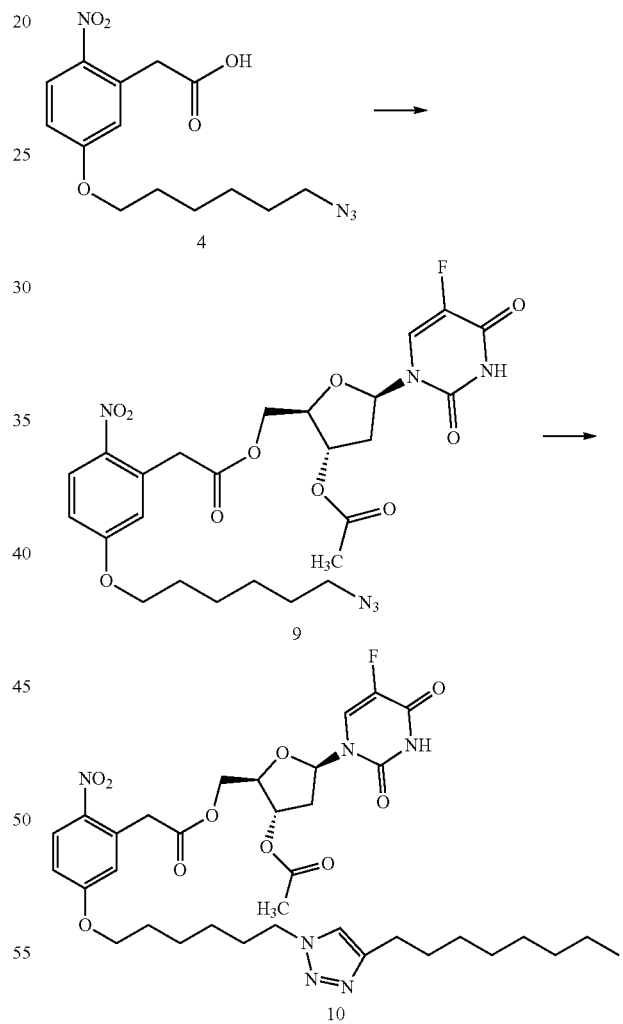

A mixture of compound 4 (390 mg, 1.21 mmol), 2-methyl-5-nitroimidazole-1-ethanol (250 mg, 1.46 mmol), 1-ethyl-3-(3-dimethylaminopropyl)carbodiimide hydrochloride (290 mg, 1.51 mmol), 4-(dimethylamino)pyridine (38 mg, 0.3 mmol), and anhydrous CH₂Cl₂ (15 mL) was stirred at room temperature under argon. The pinkish-red color of the reaction mixture faded as the mixture became homogeneous over about one hour. After 16 hr, the mixture was diluted with CH₂Cl₂ (200 mL), washed with 50% saturated NaHCO₃ solution (100 mL), 50% saturated NaCl solution (100 mL), dried over anhydrous Na₂SO₄, filtered, A mixture of compound 4 (208 mg, 0.64 mmol), 3-O-acetyl-5-fluorouridine (155 mg, 0.54 mmol), 1-ethyl-3-(3-dimethylaminopropyl)carbodiimide hydrochloride (240 mg, 1.25 mmol), 4-(dimethylamino)pyridine (30 mg, 0.25 mmol), and anhydrous CH₃CN (15 mL) was stirred at room temperature under argon. The mixture became homogeneous over about 10 min and developed a pinkish-orange color that faded with time. After 2 hr, the mixture was diluted with 50% saturated NaHCO₃ solution (200 mL), extracted with CH₂Cl₂ (2×150 mL), the extracts washed with 50% saturated NaCl solution (100 mL), dried over anhydrous Na₂SO₄, filtered, and volatiles removed in vacuo. The residue was chromatographed on silica gel 60 (100 g) eluted with 60% EtOAc/hexanes, affording the product 9 as a colorless oil homogeneous by TLC ($R_f$ 0.34, 70% EtOAc/heptane). Yield 260 mg (0.44 mmol, 81%).

To a mixture of compound 9 (260 mg, 0.44 mmol) and 1-decyne (200 μL, 153 mg, 1.1 mmol) in THF (25 mL) and water (1 mL) that had been deoxygenated for 15 min using a stream of argon were added with vigorous stirring at room temperature anhydrous cupric sulfate (60 mg, 0.38 mmol) and sodium ascorbate (120 mg, 0.61 mmol). The mixture was stirred under argon for 16 hr. Silica gel 60 (~10 g) was added to the mixture and volatiles were removed in vacuo. The silica gel was applied to the top of a silica gel 60 column (100 g) and the column eluted with 80% EtOAc/hexanes. Product 10 was obtained as a pale yellow oil homogeneous by TLC ($R_f$ 0.18, 80% EtOAc/heptane). Yield 270 mg (0.37 mmol, 84%).

The foregoing discussion of the invention has been presented for purposes of illustration and description. The foregoing is not intended to limit the invention to the form or forms disclosed herein. Although the description of the invention has included descriptions of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter. All references cited herein are incorporated by reference in their entirety.

What is claimed is:

1. A nitroreductase-releasable pro-drug having the formula:

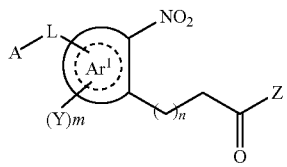

I wherein
Ar¹ is aryl or heteroaryl;
m is an integer from 0 to (t−3), wherein t is a total number of substituents possible on Ar¹;
n is 0 or 1;
Z is a pharmaceutically active compound;
Y is halide, alkyl, alkoxy, acetoxy, phenyl, or —N═N-Phenyl;
L is a linker; and
A is a carbohydrate.

2. The nitroreductase-releasable pro-drug of claim 1, wherein Ar¹ is aryl.

3. The nitroreductase-releasable pro-drug of claim 2, wherein said aryl is selected from the group consisting of phenyl, anthracenyl, naphthalenyl, and phenanthrenyl.

4. The nitroreductase-releasable pro-drug of claim 1, wherein Ar¹ is heteroaryl.

5. The nitroreductase-releasable pro-drug of claim 4, wherein said heteroaryl is selected from the group consisting of pyridinyl, furanyl, thiophenyl, pyrimidinyl, imidazoyl, and oxazolyl.

6. The nitroreductase-releasable pro-drug of claim 1, wherein n is 0.

7. The nitroreductase-releasable pro-drug of claim 1, wherein said pharmaceutically active compound comprises a drug for treating colorectal cancer, stomach cancer, inflammatory bowel disease (IBD), infectious diarrhea, intestinal bacterial infection, or intestinal bacterial overgrowth.

8. The nitroreductase-releasable pro-drug of claim 1, wherein Z is selected from the group consisting of 3-indolepropionic acid, 5-aminosalicylic acid, acetylsalicylic acid, budesonide, celecoxib, 5-fluorouracil, folinic acid, irinotecan, metformin, metronidazole, prednisolone, regorafenib, salicylic acid, and 2'-deoxy-5-fluorouridine.

9. The nitroreductase-releasable pro-drug of claim 1, wherein L is a moiety having the formula:

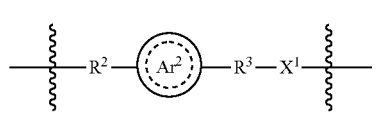

II wherein
Ar² is aryl or heteroaryl;
each of R2 and R3 is independently alkylene or heteroalkylene; and
X¹ is O, S, or NR1, wherein R1 is hydrogen, alkyl, aryl, aralkyl, heteroalkyl, cycloalkyl, cycloalkylalkyl, or oxygen.

10. The nitroreductase-releasable pro-drug of claim 9, wherein Ar² is heteroaryl.

11. The nitroreductase-releasable pro-drug of claim 9, wherein Ar² is triazolyl.

12. The nitroreductase-releasable pro-drug of claim 1, wherein A is a mono- or a disaccharide.

13. The nitroreductase-releasable pro-drug of claim 11, wherein A is a sugar selected from the group consisting of:

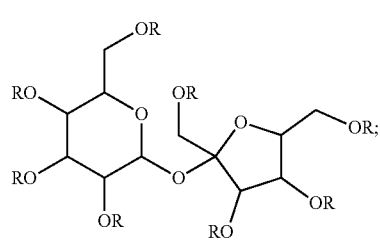

A

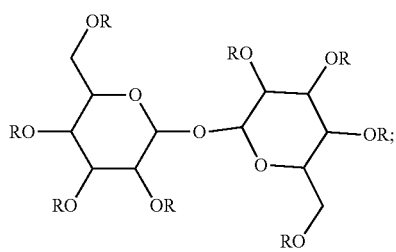

B

-continued

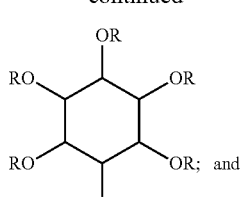

C

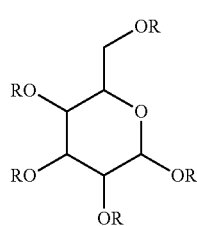

D wherein
each R is independently hydrogen, a hydroxy protecting group, an alkyl, or a moiety of the formula:

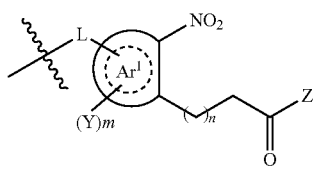

III wherein $Ar^1$, m, n, L, Y, and Z are those defined in claim 1, provided at least one of R is said moiety of formula III.

14. A nitroreductase-releasable pro-drug having the formula:

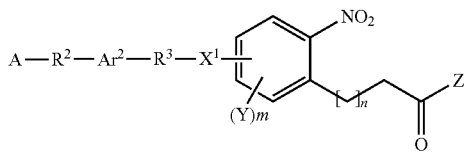

wherein
m is an integer from 0 to 3;
n is 0 or 1;
Z is a pharmaceutically active compound;
Y is halide, alkyl, alkoxy, acetoxy, phenyl, or —N=N-Phenyl;
$X^1$ is O, S, or NR1, wherein $R^1$ is hydrogen, alkyl, aryl, aralkyl, heteroalkyl, cycloalkyl, cycloalkylalkyl, or oxygen;

$Ar^2$ is heteroaryl;
each of $R^2$ and $R^3$ is independently $C_1$-$C_{20}$ alkylene or $C_1$-$C_{20}$ heteroalkylene; and
A is a monosaccharide, a disaccharide, or a carbocyclic sugar.

15. The nitroreductase-releasable pro-drug of claim 14, wherein m is 0.

16. The nitroreductase-releasable pro-drug of claim 14, wherein each of $R^2$ and $R^3$ is independently selected from the group consisting of C1-Cs alkylene and —[OCH$_2$CH$_2$]$_a$, wherein a is an integer from 1 to 5.

17. The nitroreductase-releasable pro-drug of claim 14, wherein A is selected from the group consisting of allose, altrose, glucose, mannose, gulose, idose, galactose, talose, ribose, arabinose, xylose, lyxose, psicose, fructose, sorbose, tagatose, ribulose, xylulose, myo-inositol, scyllo-inositol, muco-inositol, D-chiro-inositol, neo-inositol, L-chiro-inositol, alloinositol, epi-inositol, cis-inositol, sucrose, lactose, maltose, trehalose, cellobiose, lactulose, and chitobiose.

18. The nitroreductase-releasable pro-drug of claim 14, wherein Z is selected from the group consisting of 3-indolepropionic acid, 5-aminosalicylic acid, acetylsalicylic acid, budesonide, celecoxib, 5-fluorouracil, folinic acid, irinotecan, metformin, metronidazole, prednisolone, regorafenib, salicylic acid, and 2'-deoxy-5-fluorouridine.

19. The nitroreductase-releasable pro-drug of claim 14, wherein $Ar^2$ is 1H-1,2,3-triazolyl.

20. A method for treating colorectal cancer in a subject, said method comprising orally administering to the subject in need of treatment thereof, a therapeutically effective amount of a nitroreductase-releasable pro-drug having the formula:

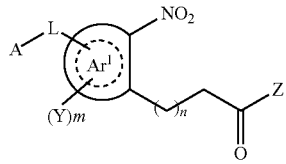

wherein
Ar1 is aryl or heteroaryl;
m is an integer from 0 to (t–3), wherein t is a total number of substituents possible on $Ar^1$;
n is 0 or 1;
Z is 5-fluorouracil:
Y is halide, alkyl, alkoxy, acetoxy, phenyl, or —N=N-Phenyl;
L is a linker; and
A is a carbohydrate.

* * * * *